(12) United States Patent
Shadduck

(10) Patent No.: US 8,900,223 B2
(45) Date of Patent: Dec. 2, 2014

(54) TISSUE ABLATION SYSTEMS AND METHODS OF USE

(75) Inventor: John H. Shadduck, Berkeley, CA (US)

(73) Assignee: Tsunami MedTech, LLC, Menlo Park, CA (US)

(*) Notice: Subject to any disclaimer, the term of this patent is extended or adjusted under 35 U.S.C. 154(b) by 969 days.

(21) Appl. No.: 12/941,778

(22) Filed: Nov. 8, 2010

(65) Prior Publication Data

US 2011/0118717 A1     May 19, 2011

Related U.S. Application Data

(60) Provisional application No. 61/259,097, filed on Nov. 6, 2009.

(51) Int. Cl.
| | |
|---|---|
| A61B 18/18 | (2006.01) |
| A61B 18/04 | (2006.01) |
| A61B 18/14 | (2006.01) |
| A61B 18/00 | (2006.01) |

(52) U.S. Cl.
CPC ............. *A61B 18/04* (2013.01); *A61B 18/1477* (2013.01); *A61B 2018/00434* (2013.01); *A61B 2018/00589* (2013.01); *A61B 2018/00601* (2013.01); *A61B 2018/048* (2013.01); *A61B 2018/1412* (2013.01)
USPC .................................. 606/27; 606/28; 606/41

(58) Field of Classification Search
USPC ................................................ 606/27–32, 41
See application file for complete search history.

(56) References Cited

U.S. PATENT DOCUMENTS

| | | |
|---|---|---|
| 408,899 A | 8/1889 | Bioch et al. |
| 697,181 A | 4/1902 | Smith |
| 1,719,750 A | 9/1927 | Bridge et al. |
| 3,818,913 A | 6/1974 | Wallach |
| 3,880,168 A | 4/1975 | Berman |
| 3,930,505 A | 1/1976 | Wallach |
| 4,024,866 A | 5/1977 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |

(Continued)

FOREIGN PATENT DOCUMENTS

| | | |
|---|---|---|
| WO | WO 00/11927 | 3/2000 |
| WO | WO 00/29055 | 5/2000 |

(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

(Continued)

*Primary Examiner* — Linda Dvorak
*Assistant Examiner* — Amanda Scott
(74) *Attorney, Agent, or Firm* — Levine Bagade Han LLP

(57) ABSTRACT

This invention relates to medical instruments and systems for applying energy to tissue. Variations of the systems and methods described herein include ablating, sealing, and extracting tissue with high pressure flows of fluids that in part utilizes a vapor-to-liquid phase change of flow media to apply thermal energy to the tissue.

22 Claims, 14 Drawing Sheets

(56) References Cited

U.S. PATENT DOCUMENTS

| | | |
|---|---|---|
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,084,043 A | 1/1992 | Hertzmann et al. |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,669,907 A | 9/1997 | Platt, Jr. et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,836,896 A | 11/1998 | Rosenschein |
| 5,843,019 A | 12/1998 | Eggers et al. |
| 5,843,073 A | 12/1998 | Sinofsky |
| 5,871,469 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwan |
| 5,989,445 A | 11/1999 | Wise et al. |
| 5,997,499 A | 12/1999 | Sussman et al. |
| 6,024,095 A | 2/2000 | Stanley, III |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Bmassengill |
| 6,110,162 A | 8/2000 | Sussman et al. |
| 6,113,722 A | 9/2000 | Hoffman et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,194 A | 12/2000 | Eggers et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |

(56) References Cited

U.S. PATENT DOCUMENTS

| | | |
|---|---|---|
| 6,315,755 B1 | 11/2001 | Sussman |
| 6,319,222 B1 | 11/2001 | Andrew et al. |
| 6,327,505 B1 | 12/2001 | Medhkour et al. |
| 6,331,171 B1 | 12/2001 | Cohen |
| 6,355,032 B1 | 3/2002 | Hovda et al. |
| 6,375,635 B1 | 4/2002 | Moutafis et al. |
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,694 B1 | 10/2002 | Massengill |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,547,810 B1 | 4/2003 | Sharkey et al. |
| 6,558,379 B1 | 5/2003 | Batchelor et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,682,543 B2 | 1/2004 | Barbut et al. |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,674 B1 | 5/2005 | Woloszko et al. |
| 6,896,675 B2 | 5/2005 | Leung et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |
| 6,921,385 B2 | 7/2005 | Clements et al. |
| 6,929,640 B1 | 8/2005 | Underwood et al. |
| 6,949,096 B2 | 9/2005 | Davison et al. |
| 6,955,675 B2 | 10/2005 | Jain |
| 6,960,182 B2 | 11/2005 | Moutafis et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,094,249 B1 | 8/2006 | Broome et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,162,303 B2 | 1/2007 | Levin et al. |
| 7,192,400 B2 | 3/2007 | Campbell et al. |
| 7,233,820 B2 | 6/2007 | Gilboa |
| 7,235,070 B2 | 6/2007 | Vanney |
| 7,311,708 B2 | 12/2007 | McClurken |
| 7,335,195 B2 | 2/2008 | Mehier |
| 7,347,859 B2 | 3/2008 | Garabedian et al. |
| 7,524,315 B2 | 4/2009 | Blott et al. |
| 7,549,987 B2 | 6/2009 | Shadduck |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,674,259 B2 | 3/2010 | Shadduck |
| 7,717,948 B2 | 5/2010 | Demarais et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,892,229 B2 | 2/2011 | Shadduck et al. |
| 7,937,143 B2 | 5/2011 | Demarais et al. |
| 7,993,323 B2 | 8/2011 | Barry et al. |
| 8,016,823 B2 | 9/2011 | Shadduck |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |

(56) References Cited

U.S. PATENT DOCUMENTS

| | | | |
|---|---|---|---|
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 8,187,269 B2 | 5/2012 | Shadduck et al. | |
| 8,313,485 B2 | 11/2012 | Shadduck | |
| 8,444,636 B2 | 5/2013 | Shadduck et al. | |
| 8,574,226 B2 | 11/2013 | Shadduck | |
| 8,579,888 B2 | 11/2013 | Hoey et al. | |
| 8,579,892 B2 | 11/2013 | Hoey et al. | |
| 8,579,893 B2 | 11/2013 | Hoey | |
| 2001/0020167 A1 | 9/2001 | Woloszko et al. | |
| 2001/0029370 A1 | 10/2001 | Hodva et al. | |
| 2001/0037106 A1 | 11/2001 | Shadduck | |
| 2002/0049438 A1 | 4/2002 | Sharkey et al. | |
| 2002/0077516 A1 | 6/2002 | Flanigan | |
| 2002/0078956 A1 | 6/2002 | Sharpe et al. | |
| 2002/0082667 A1 | 6/2002 | Shadduck | |
| 2002/0095152 A1 | 7/2002 | Ciarrocca et al. | |
| 2002/0111386 A1 | 8/2002 | Sekins et al. | |
| 2002/0128638 A1 | 9/2002 | Chauvet et al. | |
| 2002/0133147 A1 | 9/2002 | Marchitto et al. | |
| 2002/0161326 A1 | 10/2002 | Sussman et al. | |
| 2002/0177846 A1* | 11/2002 | Mulier et al. | 606/27 |
| 2002/0193789 A1 | 12/2002 | Underwood et al. | |
| 2003/0028189 A1 | 2/2003 | Woloszko et al. | |
| 2003/0040742 A1 | 2/2003 | Underwood et al. | |
| 2003/0097126 A1 | 5/2003 | Woloszko et al. | |
| 2003/0099279 A1 | 5/2003 | Venkatasubramanian et al. | |
| 2003/0109869 A1 | 6/2003 | Shadduck | |
| 2003/0130655 A1 | 7/2003 | Woloszko et al. | |
| 2003/0130738 A1 | 7/2003 | Hovda et al. | |
| 2003/0144654 A1 | 7/2003 | Hilal | |
| 2003/0158545 A1 | 8/2003 | Hovda et al. | |
| 2003/0163178 A1 | 8/2003 | Davison et al. | |
| 2003/0181922 A1 | 9/2003 | Alferness | |
| 2003/0212394 A1 | 11/2003 | Pearson et al. | |
| 2003/0212395 A1 | 11/2003 | Woloszko et al. | |
| 2003/0225364 A1 | 12/2003 | Kraft et al. | |
| 2004/0024398 A1 | 2/2004 | Hovda et al. | |
| 2004/0024399 A1 | 2/2004 | Sharps et al. | |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0049180 A1 | 3/2004 | Sharps et al. | |
| 2004/0054366 A1 | 3/2004 | Davison et al. | |
| 2004/0055606 A1 | 3/2004 | Hendricksen et al. | |
| 2004/0068256 A1 | 4/2004 | Rizoiu et al. | |
| 2004/0068306 A1 | 4/2004 | Shadduck | |
| 2004/0087937 A1 | 5/2004 | Eggers et al. | |
| 2004/0116922 A1 | 6/2004 | Hovda et al. | |
| 2004/0193150 A1 | 9/2004 | Sharkey et al. | |
| 2004/0199226 A1 | 10/2004 | Shadduck | |
| 2004/0230190 A1 | 11/2004 | Dahla et al. | |
| 2004/0254532 A1 | 12/2004 | Mehier | |
| 2005/0004634 A1 | 1/2005 | Ricart et al. | |
| 2005/0010205 A1 | 1/2005 | Hovda et al. | |
| 2005/0070894 A1 | 3/2005 | McClurken | |
| 2005/0119650 A1 | 6/2005 | Sanders et al. | |
| 2005/0166925 A1 | 8/2005 | Wilson et al. | |
| 2005/0171582 A1 | 8/2005 | Matlock | |
| 2005/0187543 A1 | 8/2005 | Underwood et al. | |
| 2005/0215991 A1 | 9/2005 | Altman et al. | |
| 2005/0222485 A1 | 10/2005 | Shaw et al. | |
| 2005/0228423 A1 | 10/2005 | Khashayar et al. | |
| 2005/0228424 A1 | 10/2005 | Khashayar et al. | |
| 2005/0240171 A1 | 10/2005 | Forrest | |
| 2005/0267467 A1 | 12/2005 | Paul et al. | |
| 2005/0283143 A1 | 12/2005 | Rizoiu | |
| 2006/0004400 A1 | 1/2006 | McGurk et al. | |
| 2006/0047291 A1 | 3/2006 | Barry | |
| 2006/0085054 A1 | 4/2006 | Zikorus et al. | |
| 2006/0100619 A1 | 5/2006 | McClurken et al. | |
| 2006/0130830 A1 | 6/2006 | Barry | |
| 2006/0135955 A1 | 6/2006 | Shadduck | |
| 2006/0142783 A1 | 6/2006 | Lewis et al. | |
| 2006/0161233 A1 | 7/2006 | Barry et al. | |
| 2006/0200076 A1 | 9/2006 | Gonzalez et al. | |
| 2006/0206150 A1 | 9/2006 | Demarais et al. | |
| 2006/0224154 A1* | 10/2006 | Shadduck et al. | 606/41 |
| 2006/0271111 A1 | 11/2006 | Demarais et al. | |
| 2007/0032785 A1 | 2/2007 | Diederich et al. | |
| 2007/0036417 A1 | 2/2007 | Argiro et al. | |
| 2007/0091087 A1 | 4/2007 | Zuiderveld | |
| 2007/0129720 A1 | 6/2007 | Demarais et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0265687 A1 | 11/2007 | Deem et al. | |
| 2008/0033493 A1 | 2/2008 | Deckman et al. | |
| 2008/0097429 A1 | 4/2008 | McClurken | |
| 2008/0103566 A1 | 5/2008 | Mehier | |
| 2008/0110457 A1 | 5/2008 | Barry et al. | |
| 2008/0114297 A1 | 5/2008 | Barry et al. | |
| 2008/0125747 A1 | 5/2008 | Prokop | |
| 2008/0132826 A1 | 6/2008 | Shadduck et al. | |
| 2008/0213331 A1 | 9/2008 | Gelfand et al. | |
| 2008/0255642 A1 | 10/2008 | Zarins et al. | |
| 2009/0036948 A1 | 2/2009 | Levin et al. | |
| 2009/0054871 A1 | 2/2009 | Sharkey et al. | |
| 2009/0062873 A1 | 3/2009 | Wu et al. | |
| 2009/0076409 A1 | 3/2009 | Wu et al. | |
| 2009/0105702 A1 | 4/2009 | Shadduck | |
| 2009/0105703 A1 | 4/2009 | Shadduck | |
| 2009/0125009 A1 | 5/2009 | Zikorus et al. | |
| 2009/0149846 A1 | 6/2009 | Hoey et al. | |
| 2009/0216220 A1 | 8/2009 | Hoey et al. | |
| 2009/0306640 A1 | 12/2009 | Glaze et al. | |
| 2009/0312753 A1 | 12/2009 | Shadduck | |
| 2010/0076416 A1 | 3/2010 | Hoey et al. | |
| 2010/0094270 A1 | 4/2010 | Sharma | |
| 2010/0114083 A1 | 5/2010 | Sharma | |
| 2010/0137860 A1 | 6/2010 | Demarais et al. | |
| 2010/0137952 A1 | 6/2010 | Demarais et al. | |
| 2010/0160905 A1 | 6/2010 | Shadduck | |
| 2010/0168731 A1 | 7/2010 | Wu et al. | |
| 2010/0168739 A1 | 7/2010 | Wu et al. | |
| 2010/0174282 A1 | 7/2010 | Demarais et al. | |
| 2010/0179528 A1 | 7/2010 | Shadduck et al. | |
| 2010/0185189 A1 | 7/2010 | Hoey | |
| 2010/0191112 A1 | 7/2010 | Demarais et al. | |
| 2010/0204688 A1 | 8/2010 | Hoey et al. | |
| 2010/0222851 A1 | 9/2010 | Deem et al. | |
| 2010/0222854 A1 | 9/2010 | Demarais et al. | |
| 2010/0249773 A1 | 9/2010 | Clark et al. | |
| 2010/0262133 A1 | 10/2010 | Hoey et al. | |
| 2010/0268307 A1 | 10/2010 | Demarais et al. | |
| 2011/0060324 A1 | 3/2011 | Wu et al. | |
| 2011/0077628 A1 | 3/2011 | Hoey et al. | |
| 2011/0112400 A1 | 5/2011 | Emery et al. | |
| 2011/0160648 A1 | 6/2011 | Hoey | |
| 2011/0264090 A1 | 10/2011 | Shadduck et al. | |
| 2012/0065632 A1 | 3/2012 | Shadduck | |

FOREIGN PATENT DOCUMENTS

| | | |
|---|---|---|
| WO | WO 03/070302 | 5/2000 |
| WO | WO 02/069821 | 9/2002 |
| WO | WO 03/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp, 159-164, Aug. 1986.

(56) References Cited

OTHER PUBLICATIONS

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3, pp. 781-787, Mar. 2001.

Moulding et al., "Preliminary studies for achieving transcervical oviduct occlusion by hot water or low-pressure steam," *Advancesin Planned Parenthood*, vol. 12, No. 2, pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.

Xia, Y. et al. "Soft Lithography," *Annu. Rev. Mater. Sci.*, vol. 28, pp. 153-184, 1998, accessed at http://www.bwfoundry.com/xia.pdf.

\* cited by examiner

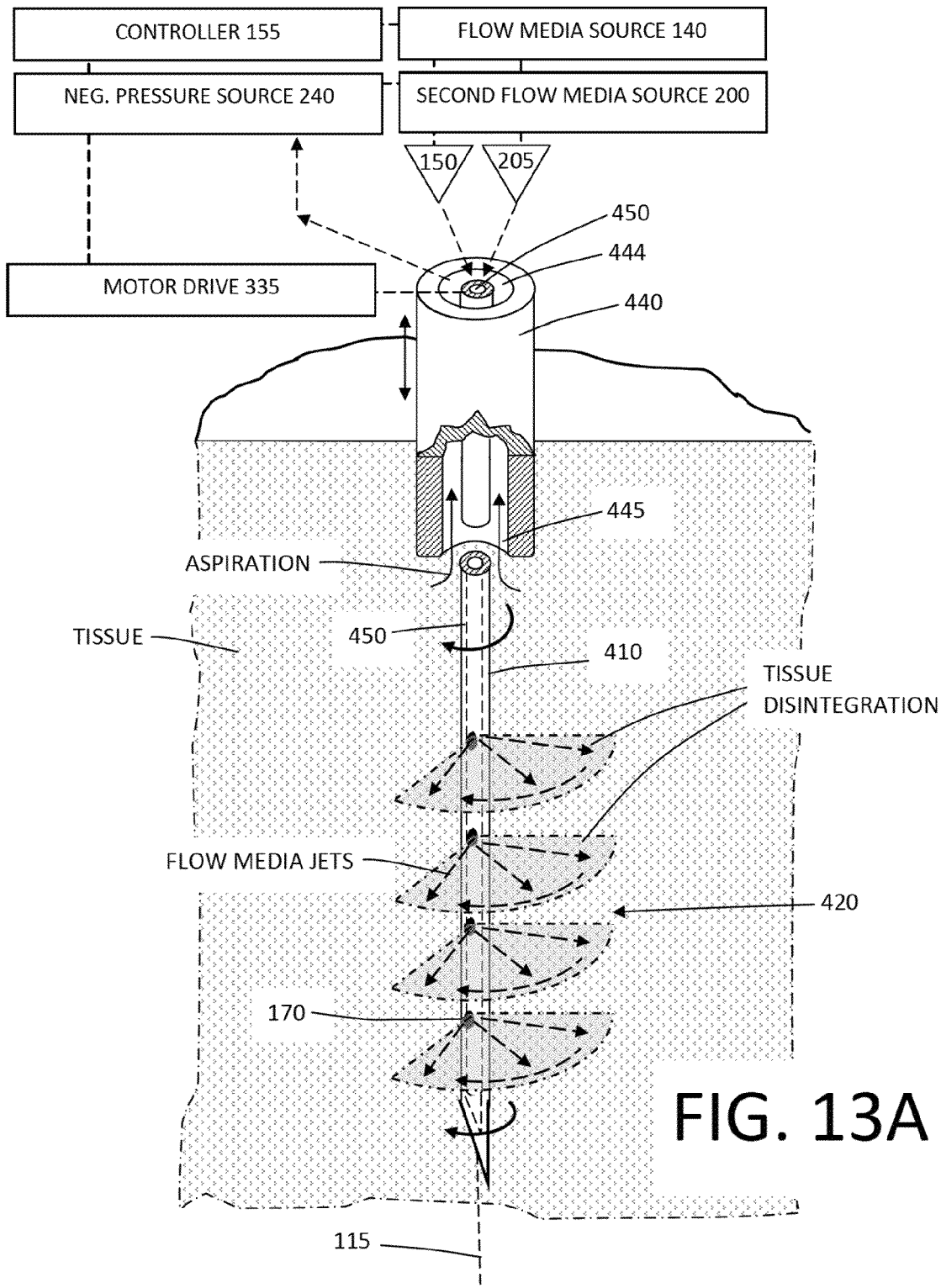

TISSUE ABLATION SYSTEMS AND METHODS OF USE

CROSS-REFERENCE TO RELATED APPLICATIONS

This application is a non-provisional of U.S. Patent Application No. 61/259,097 filed on Nov. 6, 2009, the content of which is incorporated herein by reference in its entirety.

The systems and methods described herein are also related to: U.S. Patent Provisional Application No. 61/126,647 filed May 6, 2008 entitled MEDICAL SYSTEM AND METHOD OF USE; Application No. 61/126,651 filed May 6, 2008 entitled MEDICAL SYSTEM AND METHOD OF USE; U.S. Application No. 61/126,612 filed May 6, 2008 entitled MEDICAL SYSTEM AND METHOD OF USE; Application No. 61/126,636 filed May 6, 2008 entitled MEDICAL SYSTEM AND METHOD OF USE; Application No. 61/130,345 filed May 31, 2008 entitled MEDICAL SYSTEM AND METHOD OF USE; Application No. 61/191,459 filed Sep. 9, 2008 entitled MEDICAL SYSTEM AND METHOD OF USE; Application No. 61/066,396 filed Feb. 20, 2008 entitled TISSUE ABLATION SYSTEM AND METHOD OF USE; Application No. 61/123,416 filed Apr. 8, 2008 entitled MEDICAL SYSTEM AND METHOD OF USE; Application No. 61/068,049 filed Mar. 4, 2008 entitled MEDICAL SYSTEM AND METHOD OF USE; Application No. 61/123,384 filed Apr. 8, 2008 entitled MEDICAL SYSTEM AND METHOD OF USE; Application No. 61/068,130 filed Mar. 4, 2008 entitled MEDICAL SYSTEM AND METHOD OF USE; Application No. 61/123,417 filed Apr. 8, 2008 entitled MEDICAL SYSTEM AND METHOD OF USE; Application No. 61/123,412 filed Apr. 8, 2008 entitled MEDICAL SYSTEM AND METHOD OF USE; Application No. 61/126,830 filed May 7, 2008 entitled MEDICAL SYSTEM AND METHOD OF USE; and Application No. 61/126,620 filed May 6, 2008 entitled MEDICAL SYSTEM AND METHOD OF USE.

The systems and methods described herein are also related to U.S. patent application Ser. No. 10/681,625 filed Oct. 7, 2003 entitled MEDICAL INSTRUMENTS AND TECHNIQUES FOR THERMALLY-MEDIATED THERAPIES; application Ser. No. 11/158,930 filed Jun. 22, 2005 entitled MEDICAL INSTRUMENTS AND TECHNIQUES FOR TREATING PULMONARY DISORDERS; application Ser. No. 11/244,329 filed Oct. 5, 2005 entitled MEDICAL INSTRUMENTS AND METHODS OF USE and application Ser. No. 11/329,381 filed Jan. 10, 2006 entitled MEDICAL INSTRUMENT AND METHOD OF USE.

All of the applications discussed throughout this disclosure are incorporated herein by this reference and made a part of this specification, together with the specifications of all other commonly-invented applications cited in the above applications.

FIELD OF THE INVENTION

This invention relates to medical instruments and systems for applying energy to tissue. Variations of the systems and methods described herein include ablating, sealing, and extracting tissue with high pressure flows of fluids that in part utilizes a vapor-to-liquid phase change of flow media to apply thermal energy to the tissue.

BRIEF DESCRIPTION OF THE DRAWINGS

FIG. 13A is a representational view of another working end that is moveable axially and rotationally with multiple outlets for jetting flow media to cut, ablate disintegrate and remove tissue, with the figure showing rotational movement and cutting paths.

DETAILED DESCRIPTION

Figure 1:
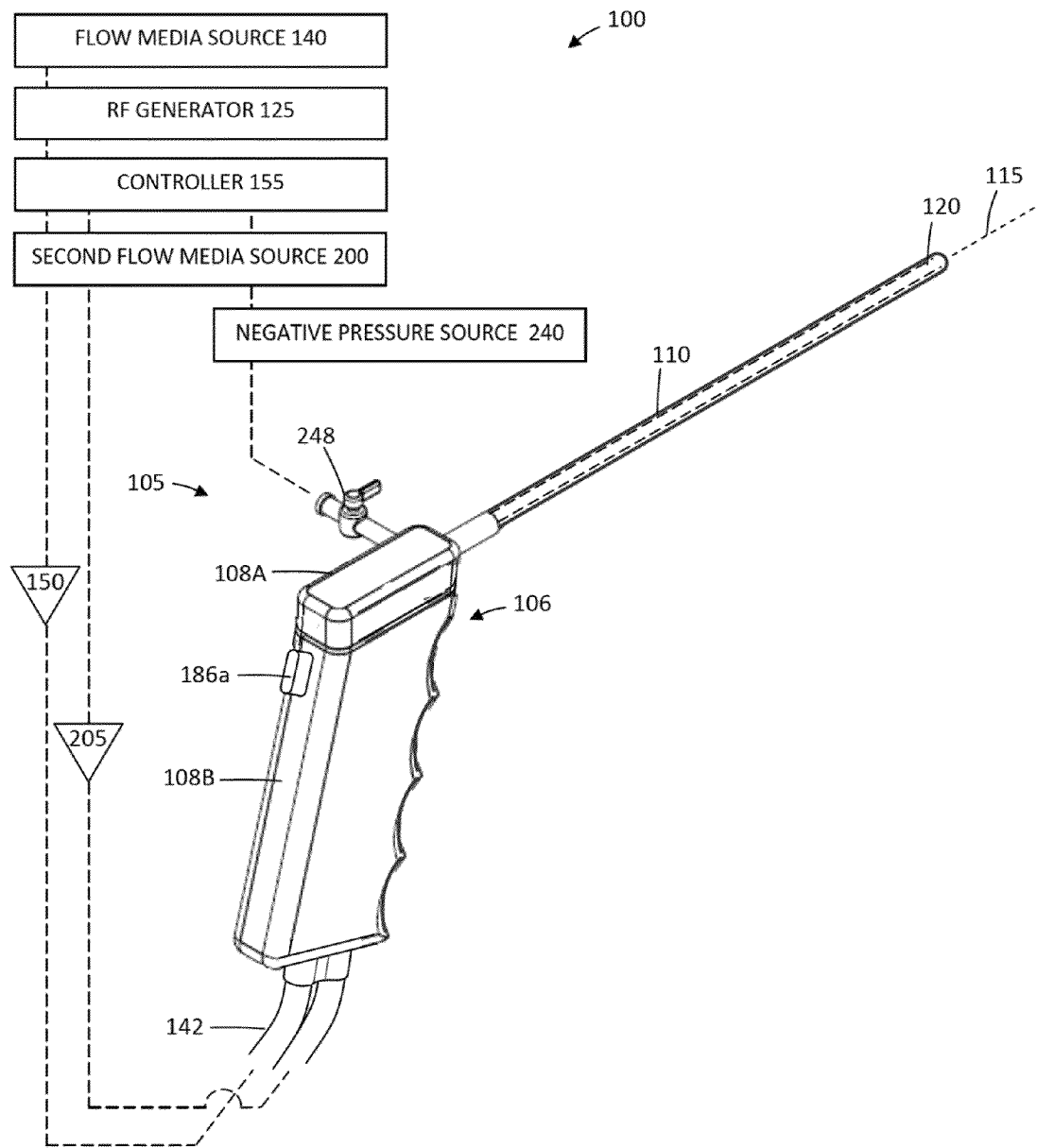
FIG. 1 is a tissue ablation system corresponding to the invention that utilizes high pressure flows of a flow media delivered into tissue from the working end of a probe to allow the controlled ablation of targeted tissue, and aspiration of ablated tissue.
Figure 2:
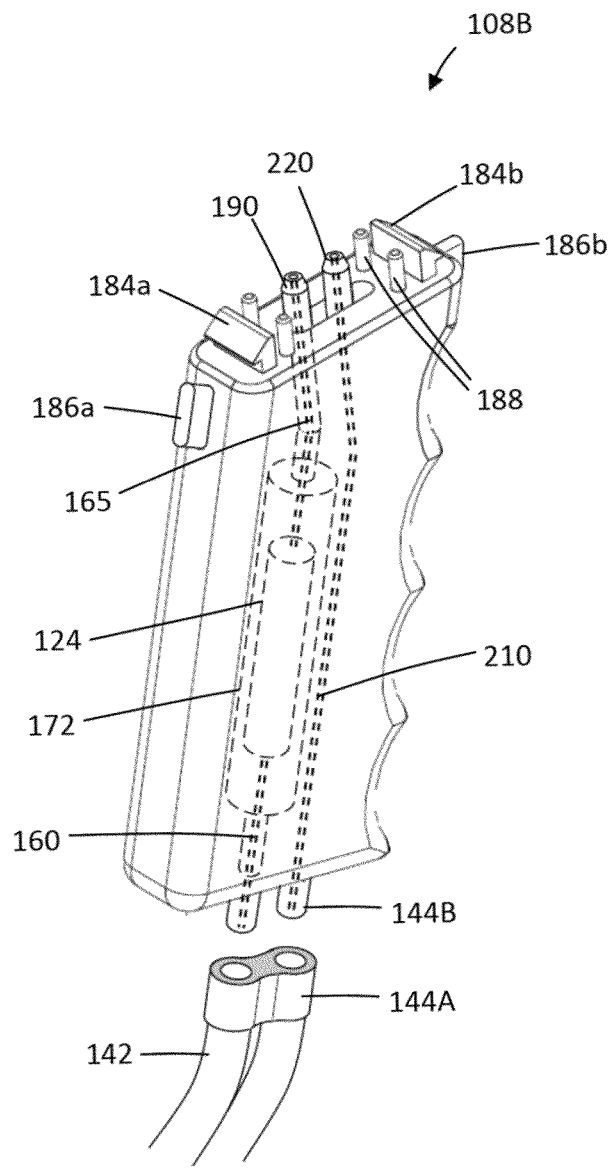
FIG. 2 is a handle component of the ablation system of FIG. 1.

FIGS. 1 and 2 depict an embodiment corresponding to the invention that provides an ablation system 100 that utilizes controlled high pressure flows of a flow media to ablate, disintegrate, seal and optionally remove tissue from a patient's body. FIG. 1 shows an ablation probe 105 that is configured with a pistol-grip handle member 106 for gripping with a human hand. The handle member 106 alternatively can be any in-line handle or other type of handle, or any proximal handle end adapted for connection to a surgical robot. In one embodiment shown in FIGS. 1 and 2, the handle comprises first and second detachable components, 108A and 108B. Handle component 108A is coupled to an elongated extension member 110 extending along a longitudinal axis 115 to a distal working end 120. The axial extension member 110 can have a suitable length and diameter for a particular ablation procedure, and can range from 1 mm to 10 mm in cross section and can be rigid, semi-rigid, deflectable, hinged or deformable. The extension member 110 also can be configured for with a channel for accommodating a rigid or flexible endoscope or a disposable optic fiber to provide viewing means for navigating the working end in the interior of a patient's body. As will be described below, the system is configured to deliver at least one flow of a flow media, such as water vapor, atomized water droplets or a jet of water in a pulsed or continuous mode, any of which can be configured to ablate tissue. The use of water vapor and fluid jets to ablate tissue has been described in the following co-pending U.S. patent applications: U.S. patent application Ser. No. 10/681,625 filed Oct. 7, 2003 titled "Medical Instruments and Techniques for Thermally-Mediated Therapies"; Ser. No. 11/158,930 filed Jun. 22, 2005 titled "Medical Instruments and Techniques for Treating Pulmonary Disorders"; Ser. No. 11/244,329 filed Oct. 5, 2005 titled "Medical Instruments and Methods of Use" and Ser. No. 11/329,381 filed Jan. 10, 2006 titled "Medical Instrument and Method of Use". All of the above applications are incorporated herein by this reference and made a part of this specification, together with the specifications of all other commonly-invented applications cited in the above applications.

The generation and delivery of a collapsible, high energy vapor for various therapeutic procedures is further disclosed in systems with remote vapor generation systems or sources in co-pending applications 60/929,632, 61/066,396, 61/068,049, or with vapor generator in a handle or working end, or combination thereof, as described in applications 61/068,130, 61/123,384, 61/123,412, 61/126,651, 61/126,612, 61/126,636, 61/126,620 all of which are incorporated herein by reference in their entirely.

Figure 3:
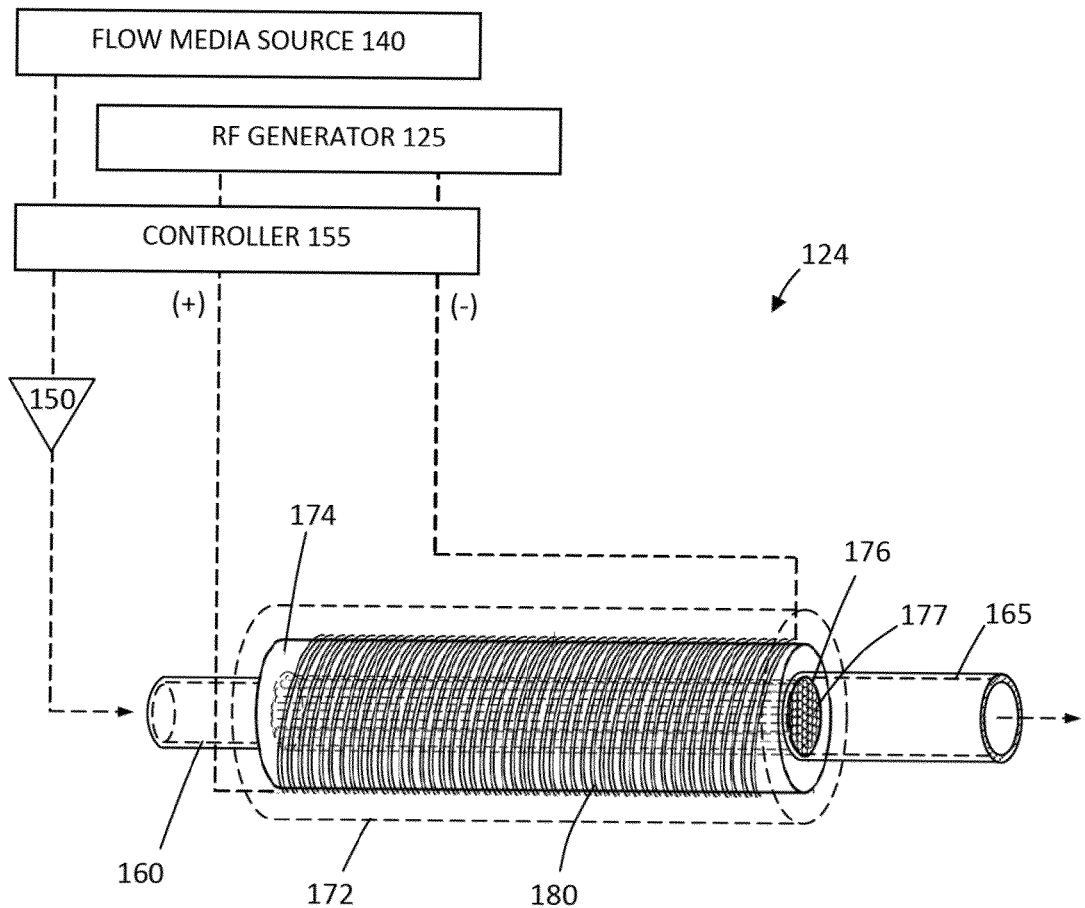
FIG. 3 is a schematic a schematic representation of an inductive heater component of the ablation system of FIG. 1 that is configured to convert a flow of liquid flow media into a flow of vapor and fluid droplets for jetting from the working end of the probe.
Figure 4A:
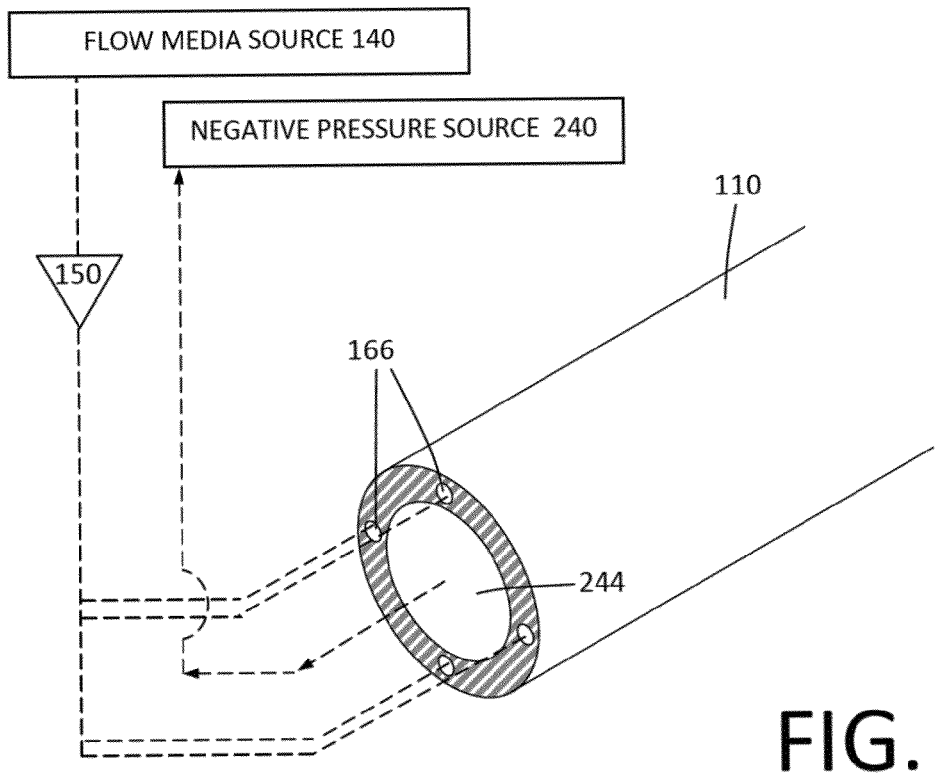
FIG. 4A is a cut-away view of the extension member of the ablation probe of FIG. 1.
Figure 4B:
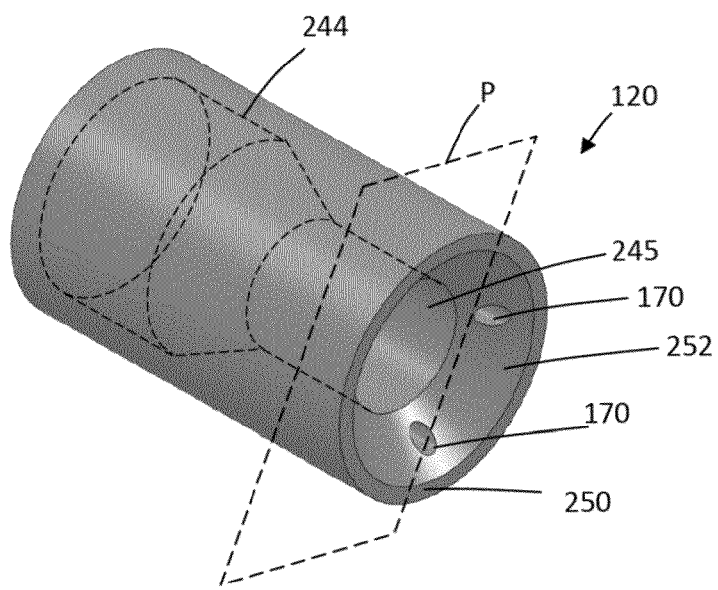
FIG. 4B is a perspective view of the working end of the ablation probe of FIG. 1.

FIGS. 1 and 2 illustrate an embodiment of tissue ablation system 100 in which detachable handle component 108B carries a heat applicator system for converting a fluid flow to a vapor flow which comprises an inductive heater assembly 124 operatively coupled to an electrical source such as an RF generator 125. The inductive heater 124 is adapted for converting a pressurized flow of a liquid, such as water or saline, into a flow of water vapor, or a pulsed flow of water vapor, atomized water droplets and/or a flow of water. The inductive heater 124 can be as described in U.S. Provisional patent application Ser. No. 12/389,808 incorporated by reference herein. In FIG. 2, it can be seen that a pressurized flow media source 140 contains the fluid or flow media 150 such as water or saline. The source 140 delivers the flow media through flexible conduit 142 and cooperating fittings 144A and 144B to handle component 108B and to inductive heater 124 (FIGS. 2 and 3). The pressurized fluid source 140 and computer controller 155 is adapted to deliver the flow media 150 at a controlled flow rate and pressure through a flow channel 160 into the inductive heater 124 and through flow channel 162 out of the inductive heater into at least one cooperating flow channel 166 in extension member 110 that communicates with at least one flow outlet 170 in the working end 120 (FIGS. 4A-4B). The flow rate of media into the inductive heater 124 can range from 0.01 ml/min to 20 ml/min and provides at pressures of between 10 psi and 10,000 psi.

As can be seen in FIGS. 2 and 3, the flow of liquid flow media 150 is directed through the inductive heater 124 that is housed in handle component 108B. The handle 106 can comprise a molded shell of a plastic and can provide an air gap or insulation 172 around the inductive heater 124. In one embodiment (FIG. 3), the inductive heater 124 comprises a ceramic cylinder 174 about 1.0" to 1.5" in length and 0.25" in diameter with a 0.10" bore 176 therein. The bore 176 contains an inductively heatable structure with a plurality of axial microchannels for receiving fluid flows which in one embodiment can be provided by a tightly-packed assembly of small diameter microtubes 177. The microtubes 177 can be any suitable material, for example any stainless steel (e.g., 316 SS) that can be instantly heated by induction. In one embodiment, the stainless steel microtubes 177 are 0.016" thin wall tubes. A winding 180 of one to ten layers having with the winding having an axial length of 1.0" is provided about the cylinder 172 for inductive heating of microtubes 177 using very high frequency current from electrical source 125. In one embodiment the winding 180 can be 26 Ga. Copper wire with a Teflon coating. It has been found that delivering at least 50 W, 100 W, 200 W, 300 W, or 400 W with suitable flow rates of water through the channels in and around the microtubes 177 can produce very high quality water vapor, for example 95% vapor or higher. An insulation layer 172 is provided about an exterior of the inductive heater, as depicted in phantom view in FIG. 3. The insulation can comprise an air or partial vacuum gap, an aerogel, insulating glass or ceramic microspheres or another insulator material. In general, the inductive heater 124 and controller 155 can be configured to produce a high quality vapor with precise parameters in terms of vapor quality, exit vapor pressure from the working end 120 and exit vapor temperature, together with maintaining the parameters within a tight range over a treatment interval. All these parameters can be controlled with a high level of precision to achieve controlled dosimetry, no matter whether a particular tissue ablation treatment calls for (i) very low pressures in tissue (e.g., 0.1 to 5 psi) over a treatment interval or (ii) very high pressures (50 psi or greater) and no matter whether the treatment interval is in the 1-10 second range or 2 to 5 minute range.

In some tissue ablation procedures, it has been found that introducing and navigating the extension member 110 and working end 120 is best accomplished by gripping handle component 108A without the laterally extending handle component 108B. The physician can also maneuver the probe 105 more easily without the additional weight and bulk of handle component 108B. For this reason, an embodiment of probe 105 can provide detachable handle components 108A and 108B. FIGS. 1 and 2, it can be seen that handle component 108B is detachably coupled to handle component 108A by first and second projecting grip-tab elements 184a and 184b that are configured to project into receiving slots in handle component 108A. Push-buttons 186a and 186b in handle 108B can be depressed to release the handle components 108A and 108B from one another. Alignment pins 188 in handle component 108B cooperate with receiving bores in handle component 108A to align the handle components when being attached to on another.

Referring to FIG. 2, a tubular projecting element 190 with flow channel 165 therein extends outwardly from handle component 108B and is configured for a fluid-tight fit in a cooperating fitting (not shown) in handle component 108A.

One or more o-rings can be used to provide a fluid-tight seal around element 190 or the flow channel 165 that extends to the working end 120.

In one embodiment depicted in FIGS. 1 and 2, a second pressurized source 200 of a second flow media 205 is coupled to a flow channel in conduit 142 and to a second flow channel 210 in handle component 108B that extends from fittings 144A and 144B to a second tubular projecting element 220 that extends outwardly from handle component 108B similar to projecting element 190. The second projecting element 220 and channel 210 therein are configured for a fluid-tight fit to a cooperating fitting and flow channel 222 in handle component 108A (not shown) that can extends through extension member 110 to working end 120 as shown in one embodiment in FIGS. 6A-6B. As can be seen in FIG. 2. the second flow media source 200 bypasses the inductive heater 124 and can deliver a flow of a gas or liquid to the working end 120 for one or more purposes, with the a continuous or pulsed flow optionally controlled by controller 155. In an embodiment, the second flow media can comprise a pharmacologic agent that is delivered to tissue from a dedicated outlet in the working end or the agent can be mixed with the heated flow media in the extension member 110 or working end 120. In another embodiment, the second flow media 205 can comprise a high pressure fluid flow that is adapted for ejection or jetting from a dedicated outlet in the working end to disintegrate tissue, or the flow can be jetted out of at least one outlet 170 (FIG. 4B) that delivers the first flow media 150. In another embodiment, the second flow media 205 can comprise a flow of gas that is adapted mixing with the heated flow media to lower its mass average temperature. In another embodiment, the second flow media can comprise a cooling gas or liquid for cooling targeted tissue or adjacent tissue after or during after an ablative treatment.

Referring to FIGS. 1, 4A and 4B, the system 100 further includes a negative pressure source 240 also controlled by controller 155 for optionally applying aspiration forces through an aspiration channel 244 in extension member 110 that extends to at least one open aspiration port 245 in the working end 120 (FIG. 4B). The negative pressure source 240 can be connected to a valved port 248 in handle component 108A that communicates with the aspiration channel 244 (FIG. 1).

Referring to FIGS. 4A-4B, it can be seen that an embodiment of working end 120 comprises a plurality of flow outlets 170 spaced apart and positioned around an open aspiration port 245. In one embodiment, a plurality of flow channels 166 in extension member 110 carry the flow media 150 to the working end 120 but a single channel can branch to the outlets or an annular channel can communicate with outlets 170. The aspiration port 245 and aspiration channel 244 are as large as possible in relation to the cross-section of extension member 110, to maximize aspiration forces at the port 245. The extension member 110 can have a cross section ranging from about 1 mm to 10 mm for various tissue ablation applications. The aspiration port 245 can be singular or plural, and can be round, oval, elongated or comprise one or more narrow slits along a blade-like edge. In The working end has a surface 250 surrounding the aspiration port 245 that is configured for contacting tissue or moving over tissue targeted for ablation. The flow outlets 170 can be disposed in surface 250 or in a recessed surface 252 that extends around port 245 that is angled or beveled relative to surface 250. The plane P of surface 250 and port 245 is 90° relative to axis 115 in the embodiment of FIGS. 4A-4B, but the angle of the plane of port 245 can be angled relative to axis 115 or parallel and offset from axis 115 as will be described below (see FIGS. 6A-6B). The flow outlets can range in number from 2 to 40 or more, and in the embodiment of FIGS. 4A-4B comprises four outlets 170. The axis 260 of media flows jetted from the flow outlets can be aligned with axis 115 or any other angle that is angled inward toward axis 115 or retrograde relative to axis 115. The flow outlets 170 range in diameter from about 0.0005 inches to 0.020 inches.

In use, the inductive heater 124 is configured to apply energy to a flow of flow media 150 to convert the media to vapor. The flow media may be provided at pressures ranging from 1 psi to 1000 psi and flow rates described above, in either a continuous flow or pulsed flows. In a method corresponding to the invention, the media flows from outlets 170 can have a predetermined vapor quality. For example when the flow media 150 is water, the vapor media may range from about 50% to 99% water vapor with the non-vapor portion comprising water droplets. By controlling the inflow pressure and flow rate from source 140, the applied energy from heater 124, the number and cross-section of outlets 170, it is possible to control the water vapor component and the water droplet component of flows jetted or ejected from outlets 170 to optimize the jetted flow media for a ablation of a particular tissue. The vapor component of the jetted media condenses to apply thermal energy to targeted tissue which will cause thermal damage, weakening and denaturation of proteins and tissue constituents. At the same time the water droplet component can apply sufficient mechanical forces to disintegrate and volumetrically remove tissue at the flow media-tissue interface. Thus, in one aspect of the invention, the quality of the vapor, i.e., the combination of jetted vapor with jetted water droplets, is configured for cutting the thermally weakened tissue while the aspiration forces through port 245 extracts and removes the tissue. By controlling the vapor quality and jetting pressure or velocity as described above, the thermal and mechanical energy applied to tissue can be modulated to discriminate between or non-ablation or tissues within a targeted tissue volume. In one method, an ablation system can be designed for treating spinal discs to ablate and extract a disc nucleus. The vapor quality and jetting velocity is controlled to discriminate between ablation of a disc nucleus and annulus. In another method, a small diameter probe can select a particular vapor quality and jetting velocity for cutting soft brain tissue without damaging microvasculature. Various neurosurgeries require cutting brain tissue without damage to tougher, elastic vasculature. In another method, a probe can use a selected vapor quality and jetting velocity for cutting any soft tissue without damaging elastic vasculature.

Figure 5:
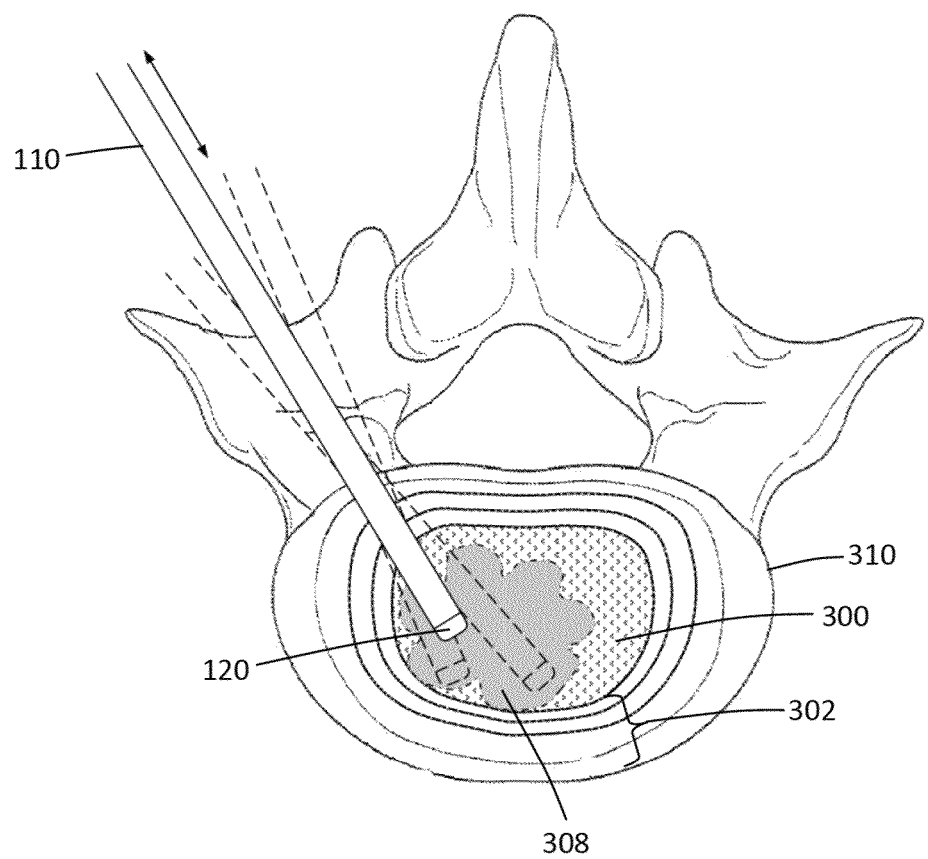
FIG. 5 is a schematic representation of a spinal disc showing the ablation probe and working end of FIG. 4B following insertion of the working end into the nucleus, and its movement to ablate and extract the gelatinous nucleus without ablating the annulus.

Referring to FIG. 5, one embodiment of system 100 is shown for use in ablating tissue in a nucleus 300 of disc 302. In various procedures to replace a disc nucleus with and artificial nucleus, or in disc decompression procedure or in a fusion procedure, it is desirable to use a tool to ablate and remove a nucleus 300 without damaging the disc annulus 310. Since the procedure is best accomplished with a small diameter probe without viewing means for viewing the targeted tissue, a probe with tissue-discrimination capabilities is needed. In the systems described above, a working end 120 as depicted in FIGS. 4B and 5 can be provided with operating parameters configured that ablate and remove the soft nucleus tissue 300 to thereby create space 308 wherein the operating parameters are not capable of ablating or cutting the disc annulus 310. In other words, the thermal energy provided by the flow and mechanical energy applied by the velocity of water or water droplets imparts energy to disintegrate soft nucleus tissue but does not impart enough energy to disintegrate tougher annulus tissue. In an embodiment configured for disc nucleus ablation, the probe extension member 110 can have a straight axis, slightly curved axis, or articulating working end and can be moved axially, angled and rotated to ablate and extract the disc nucleus as indicated schematically in FIG. 5. Minimally invasive percutaneous access to the disc is known in the art, and can use an access cannula (not shown). As will be described below, the working end 120 can have the outlets 107 and an aspiration port 245 with an distal-facing orientation, an angled orientation or a side-facing orientation.

Figure 6A:
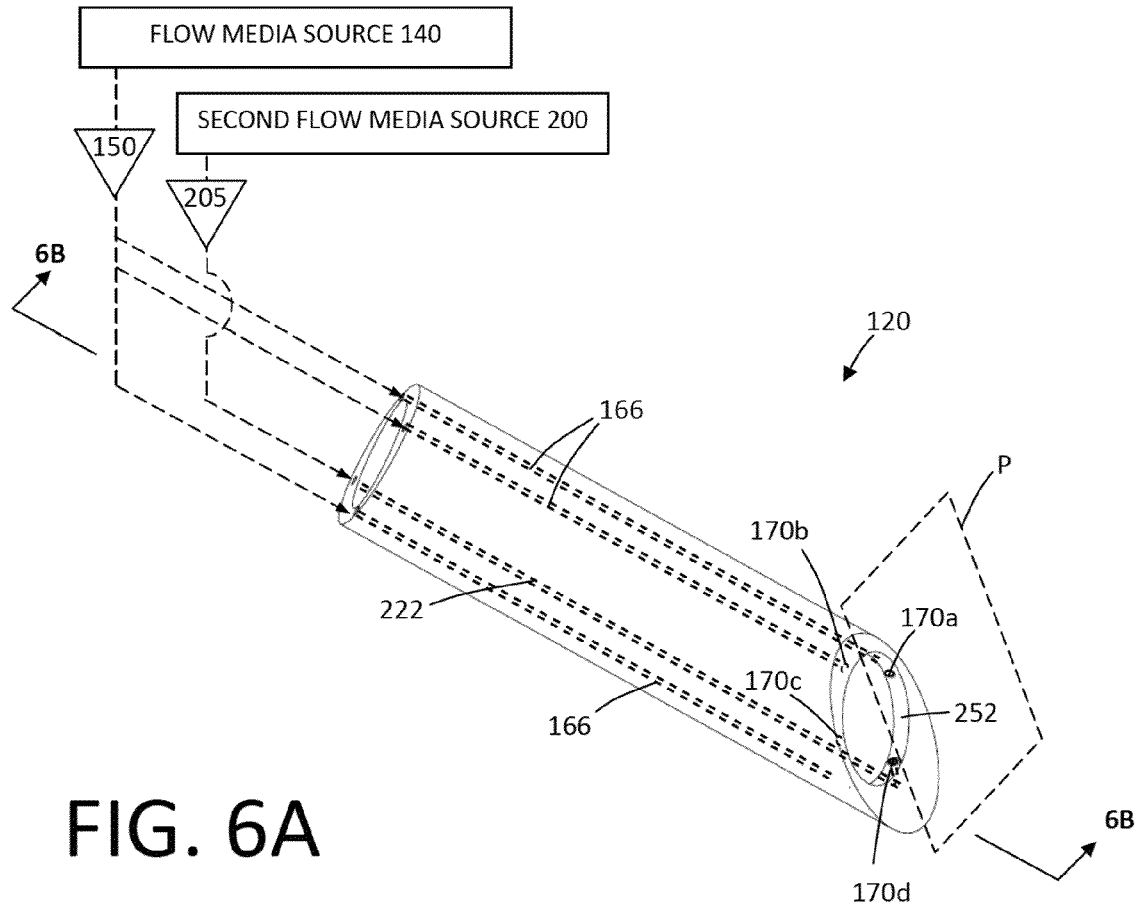
FIG. 6A is a perspective view of an alternative working end of an ablation probe similar to that of FIGS. 4A and 4B with flow outlets in an angled tissue-contacting surface and aspiration port, the flow outlets having converging axes for jetting flow media to ablate tissue.
Figure 6B:
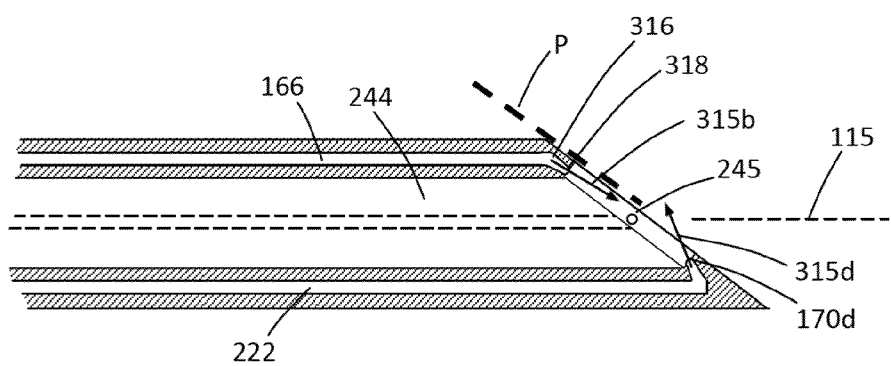
FIG. 6B is a sectional view of the working end of FIG. 6A taken along line 6B-6B of FIG. 6A showing the axes of the flow outlets coupled to first and second sources of different flow media.

FIGS. 6A and 6B are perspective and cross-section views of an alternative working end 120 of an ablation probe similar to that FIGS. 1, 4A and 4B, showing an central aspiration channel 244 and port 245 surrounded by an angled distal surface 250 that is angled relative to axis 115. The plane P of surface 250 and port 245 can range from about 30° to 90° relative to axis 115 (FIG. 6B). In this embodiment, the surface 250 is angled and configured for contacting tissue or moving over tissue targeted for ablation. In one embodiment shown in FIGS. 6A-6B, the probe extension member 110 and working end 120 are configured to eject first and second flows of flow media 150 and 205 from first flow media source 140 and second flow media source 200, respectively, to impart energy to disintegrate tissue. In the embodiment of FIGS. 6A-6B, a plurality of flow outlets 170a-170d are disposed in surface in recessed surface 252 that extends around port 245. The flow outlets 170a-170d in surface 252 can have converging axes, (e.g., axes 315a and 315b) which can be at various angles relative to surface 250 and axis 115 of the probe. As can be seen in the FIG. 6B, the flow channels 166 can have a tapered or step-region 316 that reduces the channel cross-section to a small diameter nozzle portion indicated at 318. The working end 120 of FIGS. 6A-6B can be used as shown in FIG. 5, wherein the working end can translated axially and rotated to ablate tissue both distally and to the side of working end 120. The distal tip 318 of the working end can be blunt, sharp, abrasive or serrated. In one embodiment depicted in FIGS. 6A-6B, the flow media 150 from first flow media source 140 is jetted from ports 170a-170c and can comprise a water vapor 150 produced by inductive heater 124, with the vapor media configured to condense and apply thermal energy to tissue, for reasons described above, such a weakening bonds in tissue to allow the mechanical force of jetted fluid flow 205 to more easily disintegrate tissue. The second flow media 205 can be a high pressure fluid jet that is ejected from outlet 170d and is configured to disintegrate or cut tissue.

Figure 7:
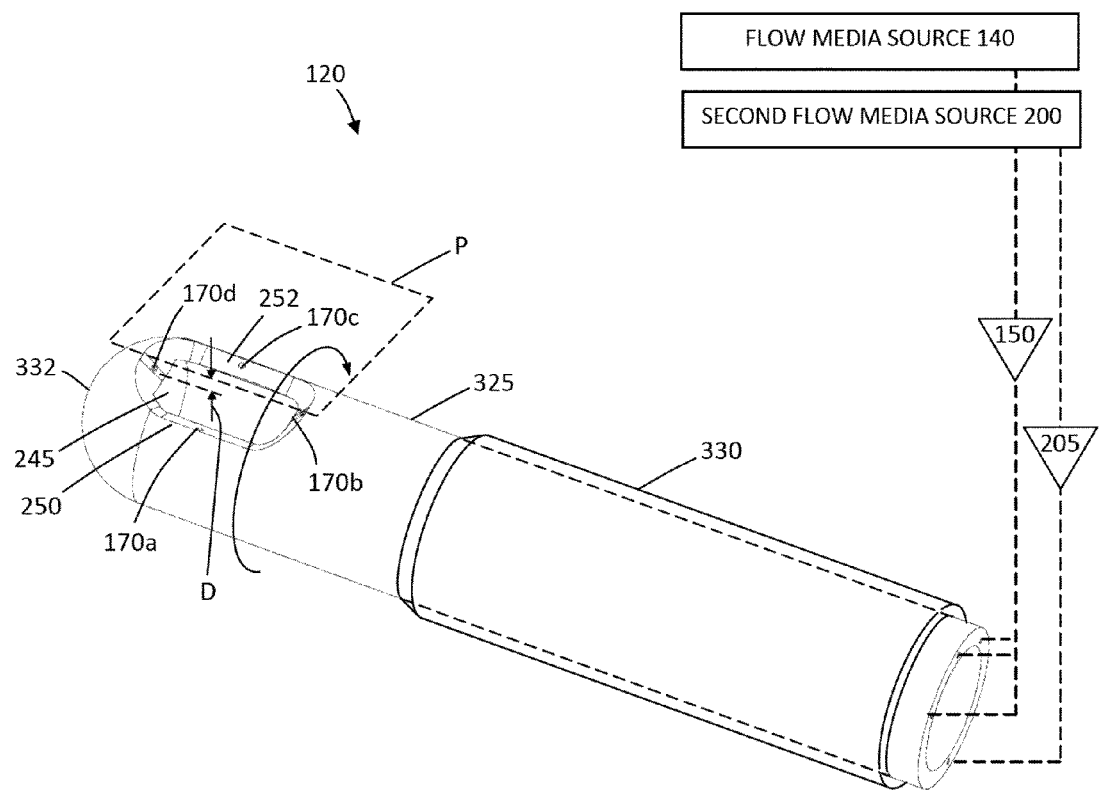
FIG. 7 is a perspective view of an alternative working end of an ablation probe similar to that of FIGS. 6A-6B with a laterally-facing tissue-ablating surface, with the aspiration port and flow media outlets having outwardly directed axes for jetting flow media to ablate tissue.

FIG. 7 is a perspective representation of an alternative working end 120 of an ablation probe that has flow media jetting features similar to that of FIGS. 6A and 6B. The working end 120 of FIG. 7 has a laterally-facing aspiration port 245 surrounded by angled surface 252 in plane P with the working end again configured with at least one flow outlet or a plurality of flow outlets 170a-170d as shown in FIG. 7. Further, the tissue-ablating surface 320 comprising the aspiration port 245 and flow outlets 170a-170d is within a motor-driven inner rotatable sleeve 325 that rotates relative to a non-rotatable outer concentric sleeve 330 that is coupled to a proximal handle. The distal end 332 of the inner sleeve 325 is shown as being blunt, but can also be a sharp penetrating tip. The inner sleeve can be rotated my any motor drive 335, such as an electric motor or air motor at speeds ranging from 10 rpm to 10,000 rpm and can be controlled by controller 155 to rotate in a continuous mode, an oscillating mode or any other continuous, pulsed or intermittent modes. In the embodiment of FIG. 7, the working end is again coupled to first and second flow media sources, 140 and 200 in communication with outlets 170a-170d for ablating tissue. The working end can have one or more flow outlets within any surface 250 or 252 of the working end in the plane P of the aspiration port 245 or inward a distance D of from 0 mm to about 5 mm from plane P.

Figure 8:
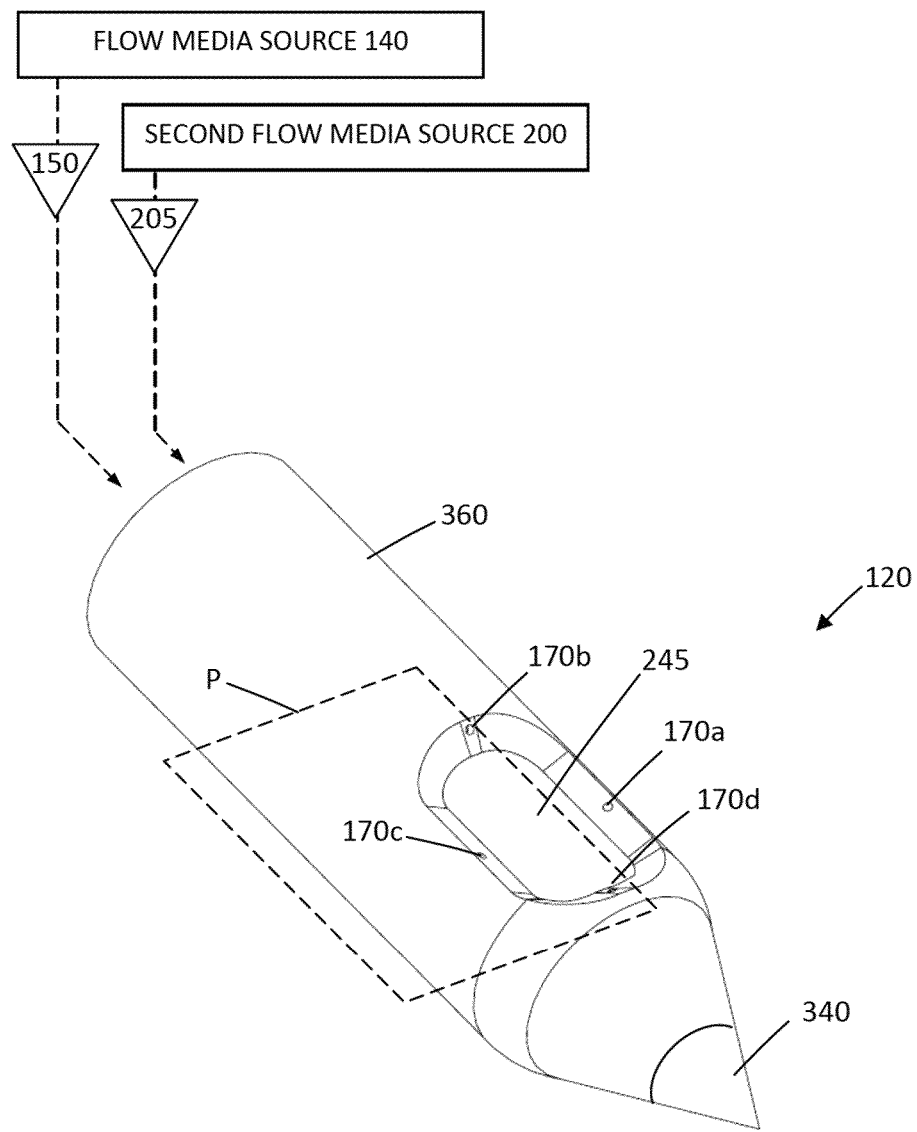
FIG. 8 is a perspective view of an alternative working end similar to that of FIG. 7 with a sharp distal comprising an RF electrode for abating tissue.

FIG. 8 is a perspective representation of an alternative working end 120 similar to that of FIGS. 6A and 7. The working end 120 of FIG. 8 can be rotatable by a motor drive or manually moved. The working end 120 of FIG. 8 further comprises a distal tip that comprises at least one RF electrode 340 for ablating tissue. In FIG. 8, the electrode 340 is a monopolar electrode that cooperates with a ground pad or return electrode on extension member 110. The distal electrode 340 can be actuated to assist in navigating or advancing the tip through tissue in the interior of a patient's body prior to using the flow media to ablate and extract tissue. The electrode 340 is operatively connected to a medical RF generator as in known in the art (not shown). In all other respects, the working end 120 of FIG. 8 would function as described previously.

Figure 9:
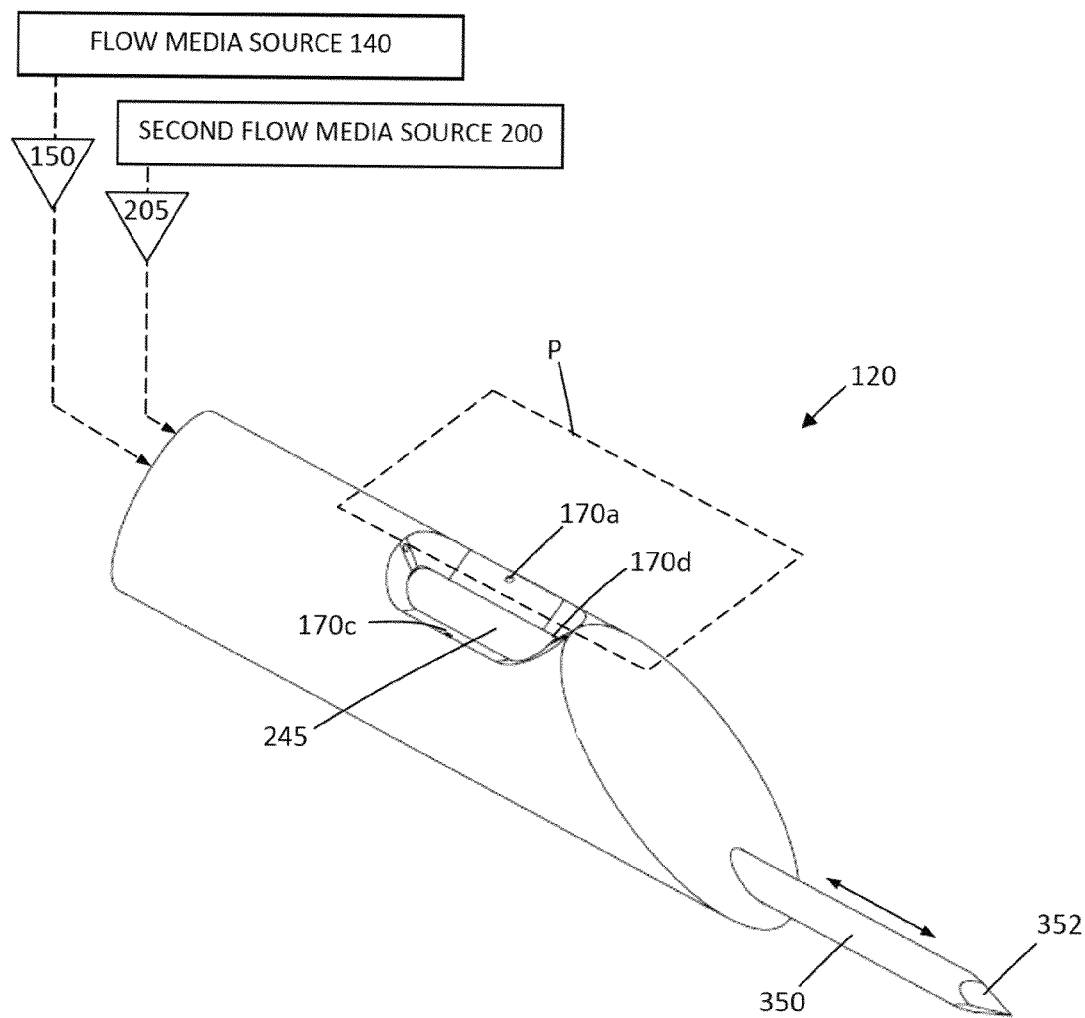
FIG. 9 is a perspective view of another working end similar to that of FIGS. 7 and 8 with extendable-retractable sharp distal for penetrating tissue.

FIG. 9 is another working end 120 similar to that of FIGS. 6A, 7 and 8 that includes an extendable-retractable member 350 with sharp tip 352 for penetrating tissue in the interior of a patient's body, for example, to reach the tissue targeted for ablation with the high pressure flow media of the invention. In all other respects, the working end 120 of FIG. 8 would function as described previously.

Figure 10:
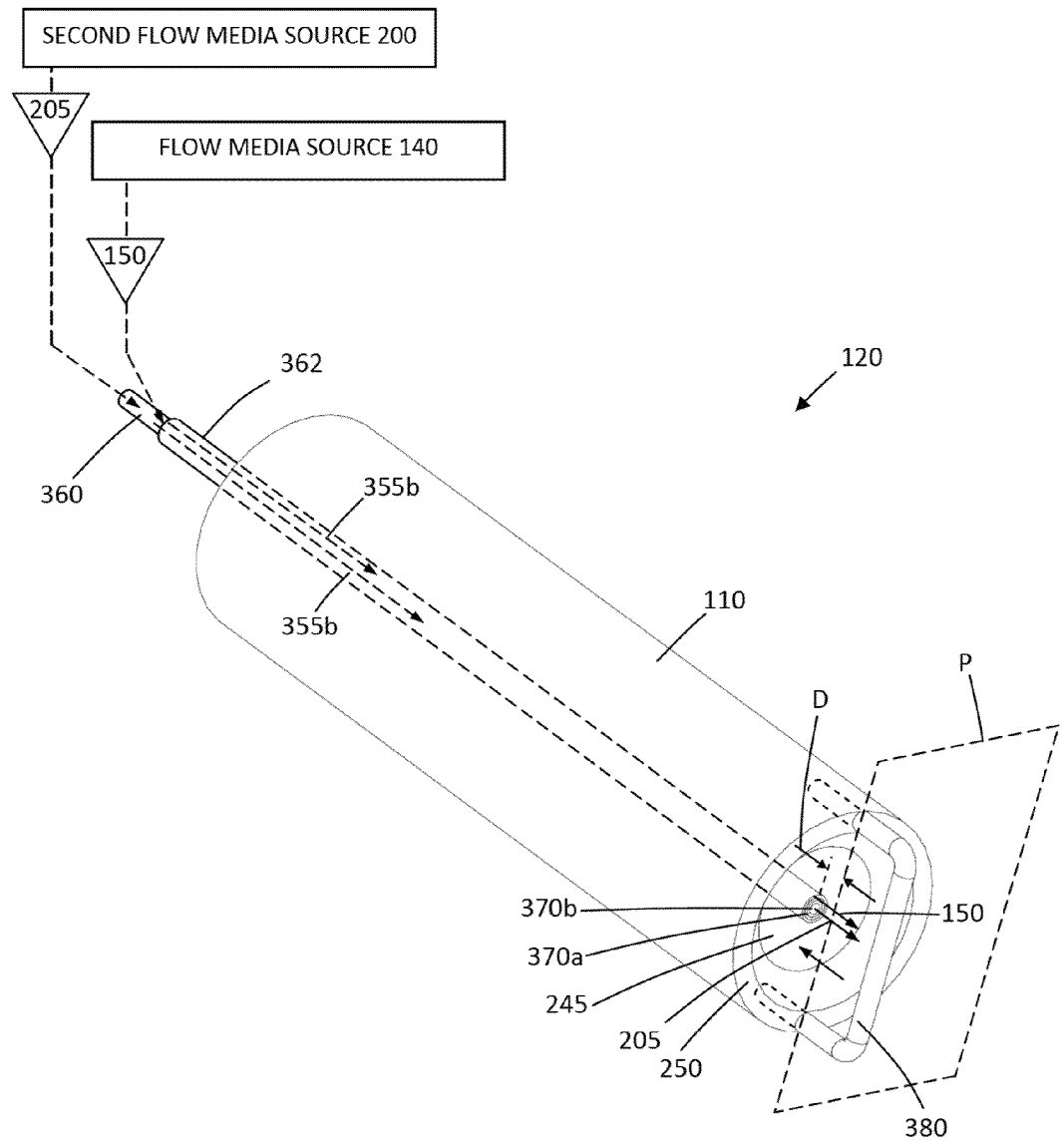
FIG. 10 is a perspective view of another working end similar to that of FIGS. 4A and 7 with concentric first and second flow outlets supported in a centrally position in an aspiration port together with a loop member for scraping tissue.

FIG. 10 is a perspective representation of another working end 120 of an ablation probe that is similar to that of FIGS. 4A-4B. In the embodiment of FIG. 10, the extension member 110 and working end 120 is coupled to first and second flow media sources, 140 and 200 in communication concentric flow channels nested outer and inner hypotubes 360 and 362 that are supported within the central portion of aspiration channel 244. The first flow media 150 can comprise a condensable vapor media for delivering thermal energy to tissue and is jetted from annular flow channel 355a and flow outlet 370a of the assembly of hypotubes 360 and 362. That is, the flow channel 355a comprises the annular lumen between outer surface of inner hypotube 362 and the inner surface of the bore of the outer hypotube 360. The second flow media 205 can comprise a fluid jet such as water for disintegrating tissue as described above, with the second media 205 jetted flow channel 355b and outlet 370b in the distal end of inner hypotube 362. The distal end of the assembly of hypotubes 360 and 362 can be positioned inward from plane P of surface 250 a distance of 0 mm to about 5 mm. The working end of the FIG. 10 also includes an optional loop member 380 that extends across the aspiration port 245 and can be used to rotate against tissue during an ablation treatment to scrape and apply additional mechanical force against tissue to be extracted. The working end of FIG. 10 further can be motor driven as the embodiment of FIG. 7 (not shown) to thus function as a device to core tissue. The loop member 380 of FIG. 10 also can comprise an extendible member that can extend from about 0 mm to 10 mm from surface 250. It also should be appreciated that all the features of the working end 120 of FIG. 10 can be configured in an angled or side-facing tissue-ablation surface as in the embodiments of FIGS. 6A and 7.

Figure 11:
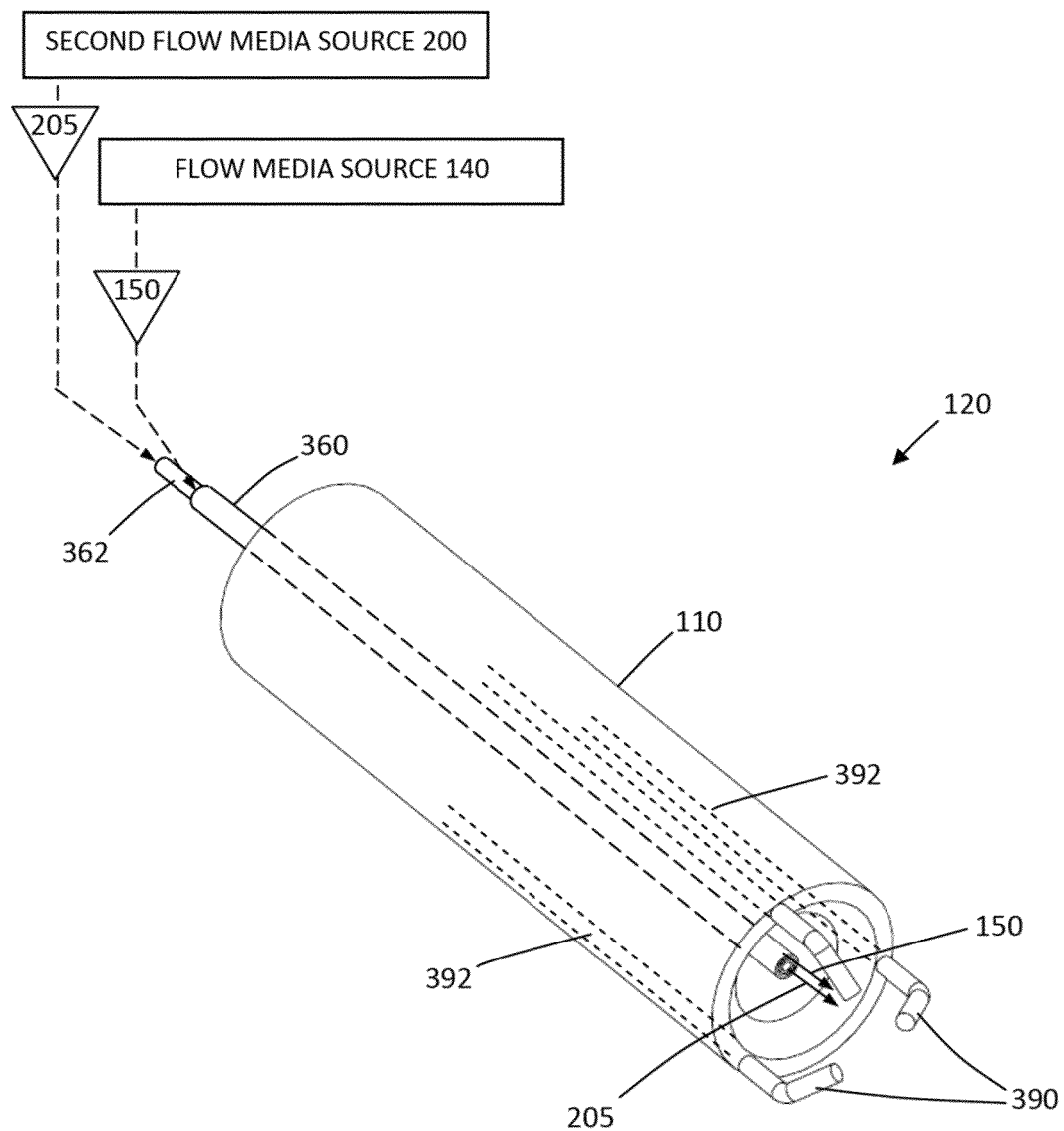
FIG. 11 is a perspective view of another working end similar to that of FIG. 10 with concentric first and second flow outlets with a surrounding aspiration port together with a plurality of brush elements for brushing tissue.

FIG. 11 is another working end 120 similar to that of FIG. 10 that includes brush elements 390 that can number from 1 to 20 that can be a flexible or substantially rigid metal or plastic and can be used for brushing tissue and can be useful in ablation and discrimination of softer and denser tissues. The brushes 390 can also be extendable and retractable in channels 392 in the working end by operation of an actuator in a handle end of the probe.

Figure 12:
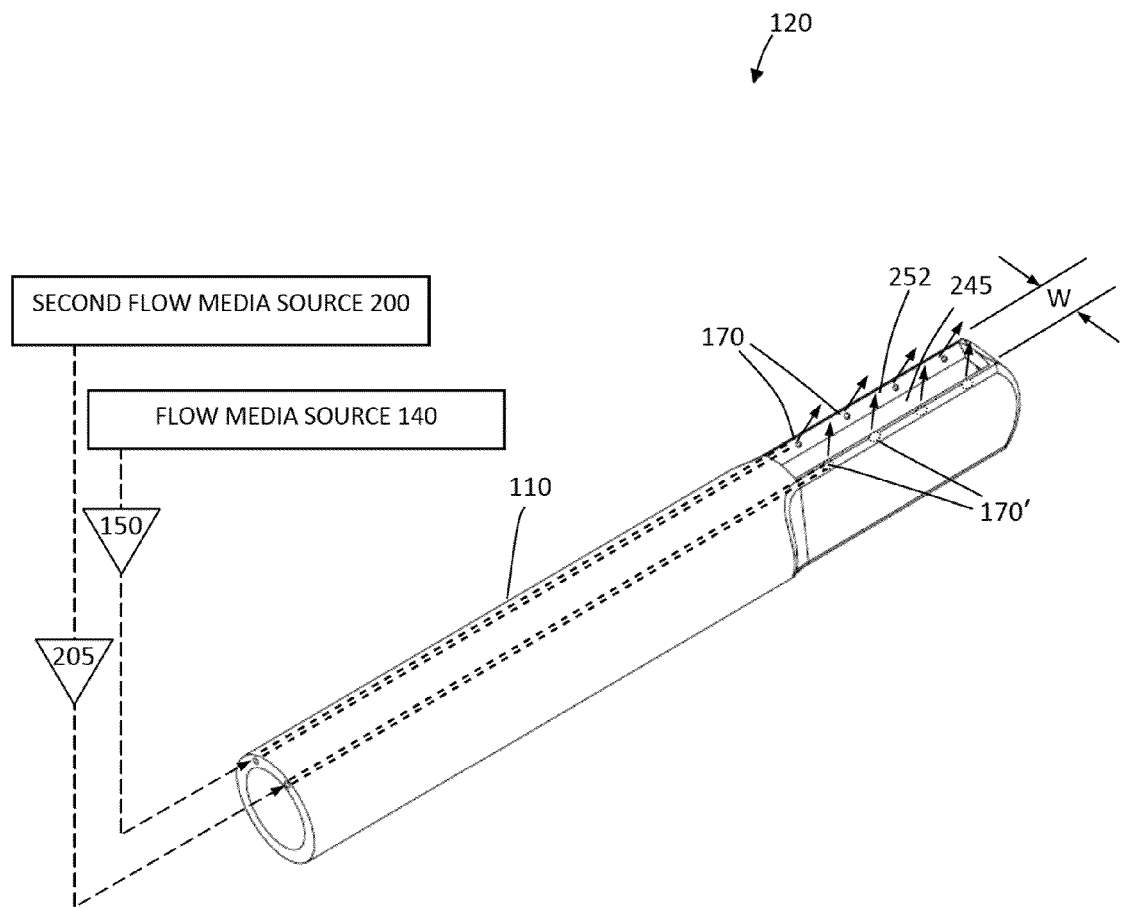
FIG. 12 is a perspective view of another working end with an elongated aspiration port in a knife-like edge and surrounding flow media outlets.

FIG. 12 is a perspective representation of an alternative working end 120 similar to those previously described that can be used as an ablative knife edge 398 to cut and coagulate tissue, for example, for use in cutting liver tissue in a liver resection procedure. The extension member 110 and working end 120 can be coupled to only a first flow media source or both first and second flow media sources, 140 and 200, as shown in FIG. 12. The first flow media source 140 can comprise a source of a condensable vapor media for delivering thermal energy to tissue that is jetted from outlets 170 (collectively) on one side of elongate aspiration port 245. The second flow media source 200 can comprise a source of a fluid that is jetted from outlets 170' (collectively) on the opposing side of aspiration port 245. The outlets 170 and 170' can range in number from about 1 to 20. The width W of the knife edge 398 can range from about 0.2 mm to 5 mm. The length of the aspiration channel 245 can range from 1 mm to 10 mm and can be in curved or straight surfaces 252 about the aspiration port 245.

Figure 13B:
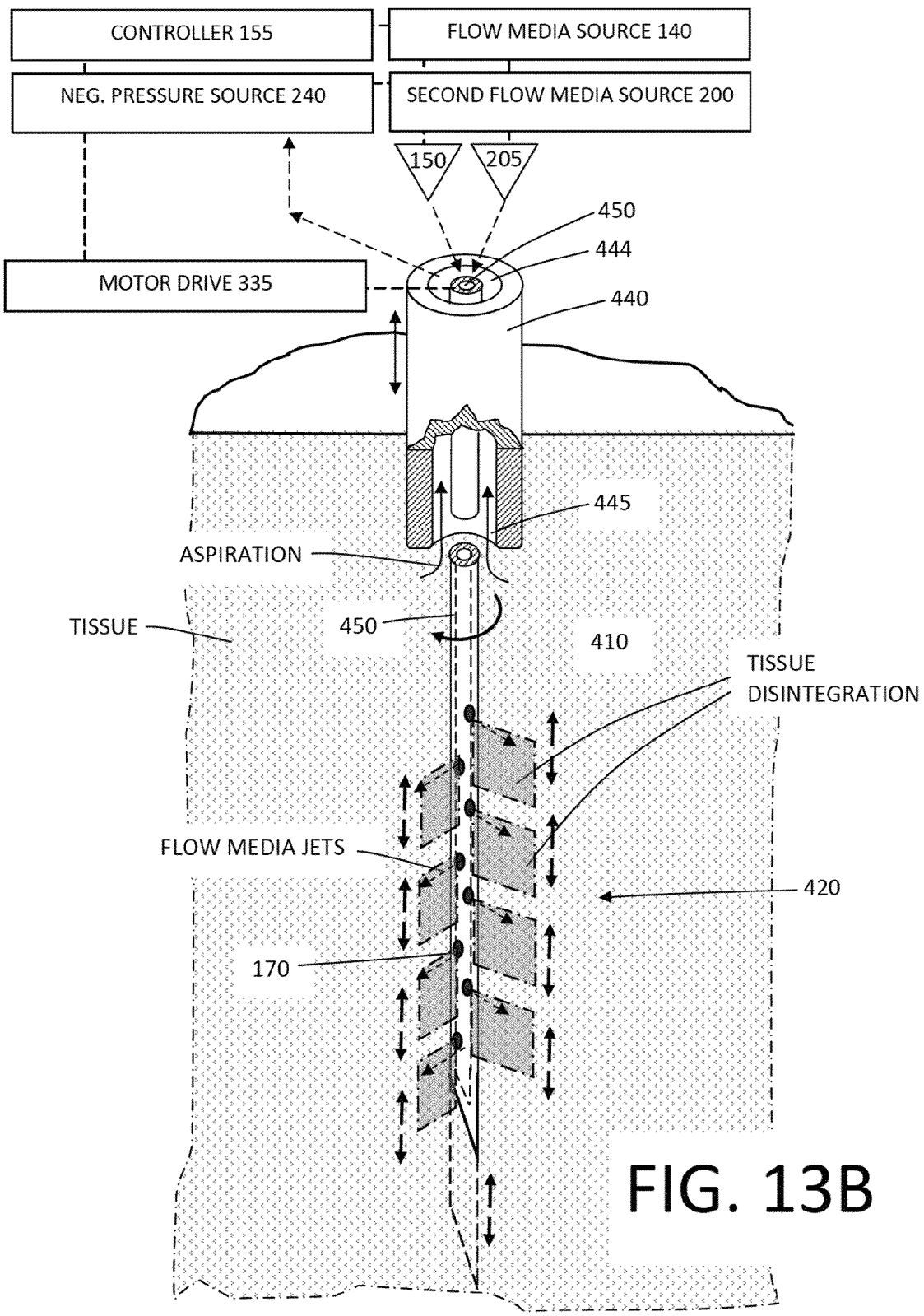
FIG. 13B is another view of the working end of FIG. 13A showing axial movement and cutting paths.

In another embodiment, referring to FIGS. 13A and 13B, an ablation system 400 can have an extension member 410 and working end 420 that has at least one flow outlet 170 for jetting flow media at a pressure and velocity configured to disintegrate or cut tissue. Like the working ends of FIGS. 7, 10 and 11 above, the working end 420 of FIG. 13A is rotatable at from 10 rpm to 10,000 rpm and by means of a motor drive 335 and controller 155. As can be seen in FIG. 13B, the working end 420 also is moveable axially by means of the motor drive and controller 155. Thus, the motor drive 335 and controller 155 can move the working end and flow outlets 170 in any pattern or sequence of angular, axial or helical motion to disintegrate, cut and ablate tissue.

In one aspect of the invention, the angular or axial movement of the flow outlet or outlets is controlled by controller 155 to limit the depth of tissue disintegration or cutting. It can be understood that at a selected flow pressure, fluid mass and flow velocity, the jetting of flow media can be configured to cut a selected depth until the flow pressure, velocity and mass is diminished and dispersed so as to longer disintegrate tissue. For example, in one embodiment, the jetted flow media from outlets 170 can have a flow pressure, mass and velocity that disintegrates tissue to a depth of 0.5 mm/s for a predetermine width of jetted flow media. In this embodiment, the working end 420 can have a circumference of 3.0 mm. Thus, rotating the working end of FIG. 13A and outlet at 60 rpm can provide a depth of tissue disintegration of 0.05 mm in a 360° path for each revolution adjacent the flow outlet. By higher speed rotation, the depth of tissue disintegration can be controlled to provide selected thin depths of ablation. By rotating in a helical pattern, an elongated tissue disintegration and ablation can be provided adjacent each flow outlet.

Thus, on aspect of a method of the invention is to controllably rotate a working end outlet that jets flow media so that tissue is disintegrated to a depth of less than 1.0 mm for each 360° revolution of the outlet, or less than 0.5 mm for each 360° revolution of the outlet or less than 0.1 mm for each 360° revolution of the outlet. The method further comprises using a plurality of jets of flow media about parallel axes or converging axes as in the device of FIG. 7.

Referring to FIGS. 13A and 13B, the working end 420 also includes an extendable-retractable sleeve 440 with aspiration channel 444 and aspiration port 445 therein. It can be understood that the sleeve 440 can be moved over the region of flow outlets 170 to remove disintegrated tissue and flow media. The negative pressure source 240 communicates with aspiration channel 444 as in previous embodiments. In other embodiments, the distal end 448 of sleeve 440 and aspiration port 445 can be distally-facing, angled or the rotatable extension member 410 can be within a side-facing aspiration port as in the embodiments of FIGS. 7-9 above.

In another aspect of the invention in FIGS. 13A and 13B, it can be seen that first and second flow media sources 140 and 200 are coupled to at least one flow channels 450 in extension member to deliver first and second flow media 150 and/or 205 through outlets 170. In one embodiment, flows of the first and second media 150 and 205 are jetted through a single channel 450 in successive intervals to disintegrate and seal tissue outward of outlets 170. In another embodiment, a first media 150 comprising a water vapor is flowed continuously and a second media of liquid water is pulsed from outlets 170. In another embodiment, two independent flow channels are provided in the extension member 410 that leads to independent flow outlets 170 (not shown).

In another aspect of the invention, the working end 420, flow media sources 140 and 200 and controller 155 can provide a first controlled pressure that is greater than 5 psi, 10 psi, 20 psi, 30 psi, 40 psi, 50 psi, 100 psi, 200 psi, 500 psi or 1000 psi for disintegrating or cutting tissue. The flow media can be any high quality vapor, low quality vapor, water or saline solution. In such an embodiment, the system can provide a second controlled pressure that is less than 50 psi, 40 psi, 30 psi, 20 psi, 10 psi and 5 psi. In use, the flow media at the second controlled pressure applies heat for sealing tissue about the disintegrated tissue region.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of treating tissue, the comprising:
positioning a probe working end in an interface with tissue;
ejecting a high pressure flow of flow media from a working end outlet, wherein the flow comprises at least in a part a condensable vapor, and wherein the flow has a selected pressure and velocity that disintegrates tissue; and
controllably rotating the working end at a selected speed to control the depth of disintegration of tissue proximate the outlet.

2. The method of claim 1 wherein the high pressure flow is jetted from a plurality of outlets at or along the working end.

3. The method of claim 1 wherein the flow media is selected from the group of water vapor, atomized water droplets, water and a pharmacological agent.

4. The method of claim 1 wherein the working end is rotated so that tissue is disintegrated to a depth of less than 1 mm for each 360° revolution of the outlet.

5. The method of claim 1 wherein the working end is rotated so that tissue is disintegrated to a depth of less than 0.5 mm for each 360° revolution of the outlet.

6. The method of claim 1 wherein the working end is rotated at a rate so that tissue is disintegrated to a depth of less than 0.1 mm for each 360° revolution of the outlet.

7. The method of claim 1 wherein the working end is rotated at a rate so that tissue is disintegrated to a depth of less than 1 mm for each 360° revolution of the outlet.

8. The method of claim 1 wherein the working end is rotated at a rate so that tissue is disintegrated to a depth of less than 0.5 mm for each 360° revolution of the outlet.

9. The method of claim 1 wherein the working end is rotated at a rate so that tissue is disintegrated to a depth of less than 0.1 mm for each 360° revolution of the outlet.

10. The method of claim 1 wherein the working; end is rotated between a rate of 10 rpm to 10,000 rpm.

11. The method of claim 1 further comprising removing disintegrated tissue through an aspiration port communicating with an aspiration channel in the probe.

12. The method of claim 1 wherein the condensable vapor applies heat to seal tissue.

13. The method of claim 1 wherein the working end has a longitudinal axis and flow media is ejected at an angle relative to the axis.

14. A method of tissue ablation, comprising:
positioning a probe working end in an interface with a tissue volume containing first and second tissue types;
ejecting at least one high pressure flow of flow media from the probe working end, wherein a flow comprises at least in a part a condensable vapor that applies energy capable of sealing tissue, wherein the flow has a selected pressure and velocity that applies energy that discriminates disintegration of tissue between the first and second tissue types,
moving the working end axially and/or rotationally contemporaneous with ejecting flow media; and
removing disintegrated tissue through an aspiration port communicating with an aspiration channel in the probe.

15. The method of claim 14 wherein at least two flow of different flow media are ejected from the working end.

16. The method of claim 15 wherein different flow media are selected from the group of water vapor, atomized water droplets, water and a pharmacological agent.

17. The method of claim 14 wherein the flow media is ejected from a plurality of outlets in the working end.

18. The method of claim 14 wherein the flow media is ejected from at least one outlet that is recessed within, the aspiration port.

19. The method of claim 14 wherein the flow media is pulsed.

20. The method of claim 14 wherein a computer controller and motor controllably moves the working end.

21. The method of claim 14 wherein a computer controller controls parameters of the ejection of flow media.

22. The method of claim 14 further comprising imaging the flow of flow media.

* * * * *